United States Patent [19]

Noiles

[11] Patent Number: 4,576,167

[45] Date of Patent: Mar. 18, 1986

[54] SURGICAL STAPLER APPARATUS WITH CURVED SHAFT

[75] Inventor: Douglas G. Noiles, New Canaan, Conn.

[73] Assignee: United States Surgical Corporation, Norwalk, Conn.

[21] Appl. No.: 299,106

[22] Filed: Sep. 3, 1981

[51] Int. Cl.[4] ............................................. A61B 17/11
[52] U.S. Cl. .................................. 128/334 R; 227/19; 227/DIG. 1
[58] Field of Search ............... 128/334 R, 334 C, 305, 128/772, 4, 5, DIG. 9; 227/19, DIG. 1; 74/501 P

[56] References Cited

U.S. PATENT DOCUMENTS

| | | | |
|---|---|---|---|
| 2,707,783 | 5/1955 | Sullivan | 1/49.1 |
| 3,080,564 | 3/1963 | Strekopitov et al. | 1/50 |
| 3,193,165 | 7/1965 | Akhalaya et al. | 227/8 |
| 3,217,557 | 11/1965 | Martinot | 74/501 P X |
| 3,252,643 | 5/1966 | Strekopytov et al. | 227/109 |
| 3,269,630 | 8/1966 | Fleischer | 227/107 |
| 3,388,847 | 6/1968 | Kasulin et al. | 227/19 |
| 3,452,615 | 7/1969 | Gregory | 74/501 |
| 3,494,533 | 2/1970 | Green et al. | 227/19 |
| 3,552,626 | 1/1971 | Astafiev et al. | 227/76 |
| 3,589,589 | 6/1971 | Akopov | 227/153 |
| 3,593,903 | 7/1971 | Astafiev | 227/76 |
| 3,638,652 | 2/1972 | Kelley | 128/305 |
| 3,692,224 | 9/1972 | Astafiev et al. | 227/19 |
| 3,795,034 | 3/1974 | Strekopytov et al. | 29/212 D |
| 3,807,407 | 4/1974 | Schweizer | 128/334 R |
| 3,935,981 | 2/1976 | Akopov et al. | 227/19 |
| 3,960,143 | 6/1976 | Terada | 128/4 |
| 4,166,466 | 9/1979 | Jarvik | 128/325 |
| 4,207,898 | 6/1980 | Becht | 128/305 |
| 4,304,236 | 12/1981 | Conta et al. | 128/325 |
| 4,319,576 | 3/1982 | Rothfuss | 128/305 |
| 4,325,376 | 4/1982 | Klieman et al. | 128/325 |

FOREIGN PATENT DOCUMENTS

| | | |
|---|---|---|
| 1082552 | 7/1980 | Canada . |
| 1057729 | 5/1959 | Fed. Rep. of Germany . |
| 1241577 | 8/1971 | United Kingdom . |

OTHER PUBLICATIONS

Brochure of YUFU Medical, Inc. showing curved instruments for esophago-gastro anastomosis, prior to 2/8/79.
Japanese brochure showing straight instrument apparently for gastro-intestinal anastomosis.
"Information Booklet for Auto Suture ® Model EEA Surgical Stapling Instrument and Disposable Loading Units", U.S. Surgical Corp., 1/79.

Primary Examiner—Michael H. Thaler
Attorney, Agent, or Firm—Robert R. Jackson; John E. Nathan

[57] ABSTRACT

A surgical stapler including a stapling assembly, an actuator assembly remote from the stapling assembly, and a longitudinal shaft assembly having a longitudinally curved section for connecting the actuator assembly to the stapling assembly and for transmitting the forces and motions required to operate the stapling assembly from the actuator assembly to the stapling assembly.

3 Claims, 16 Drawing Figures

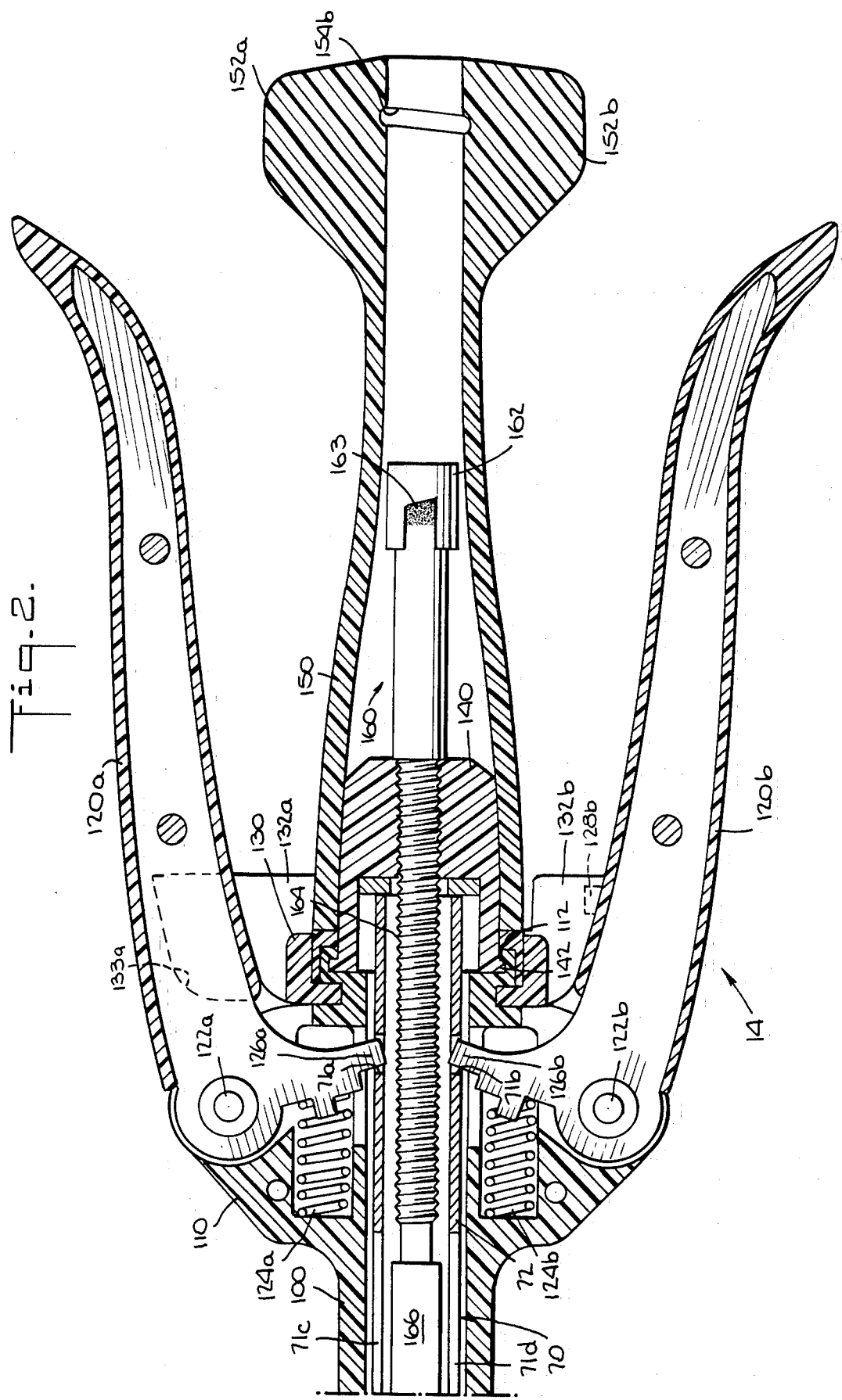

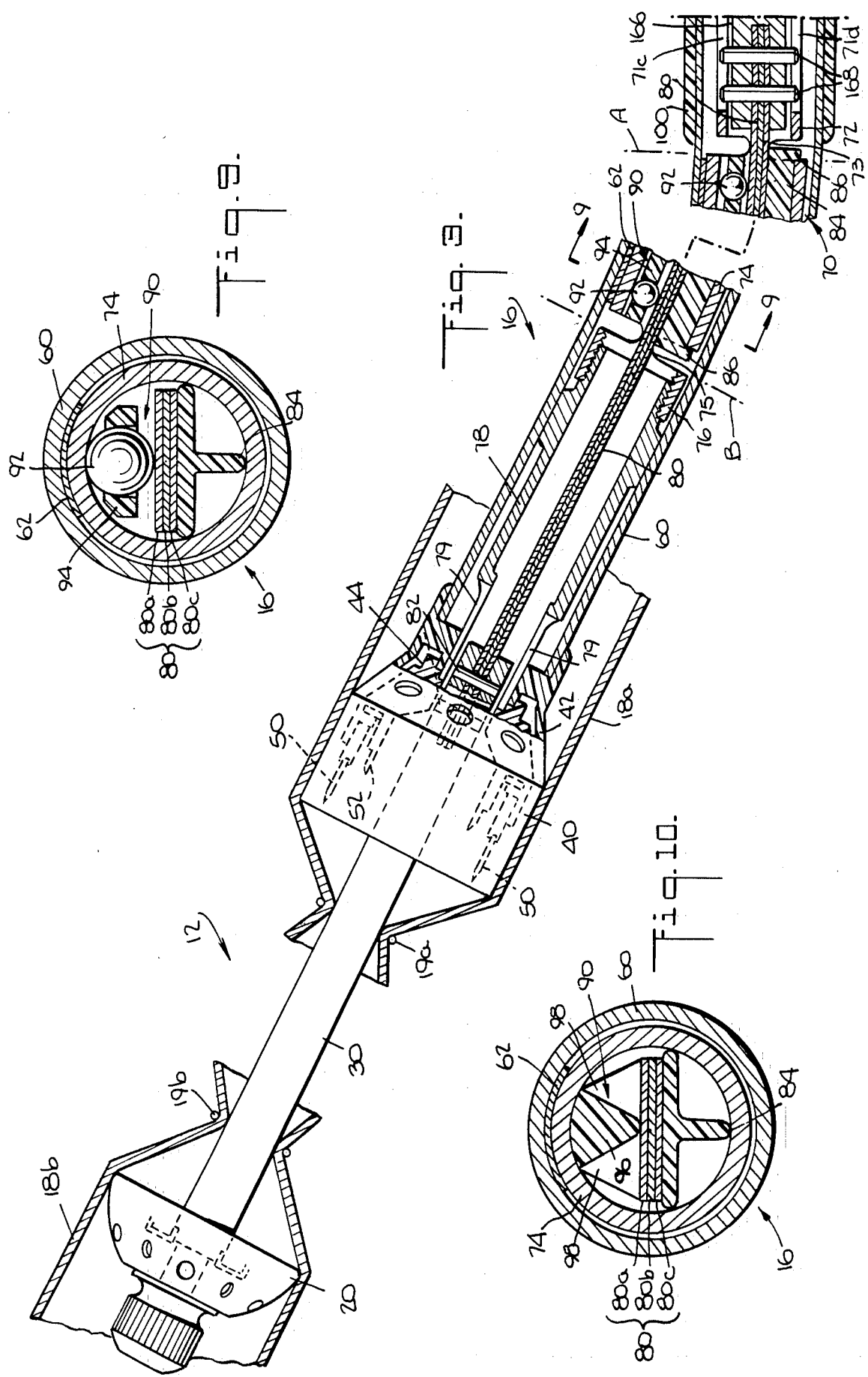

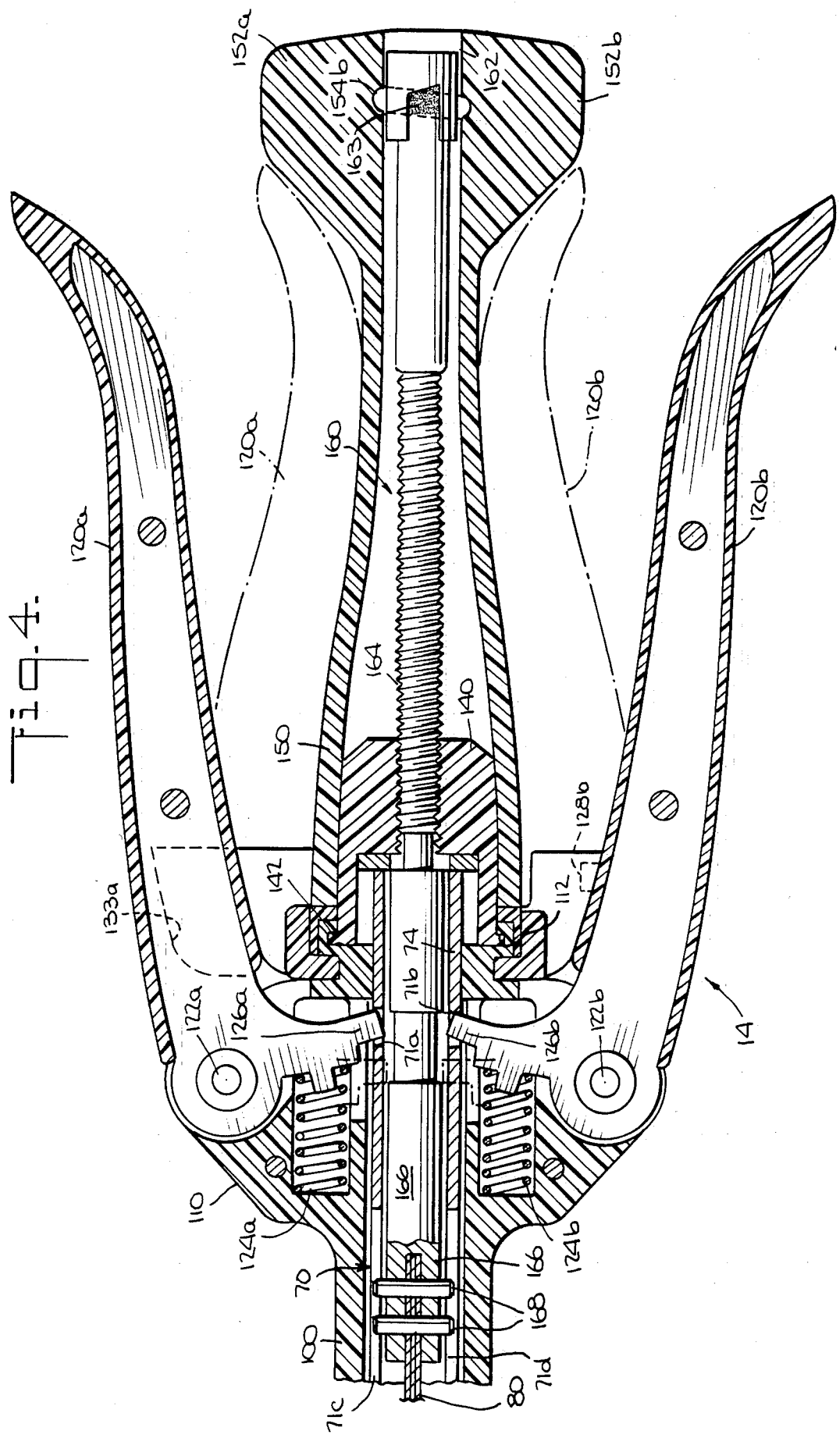

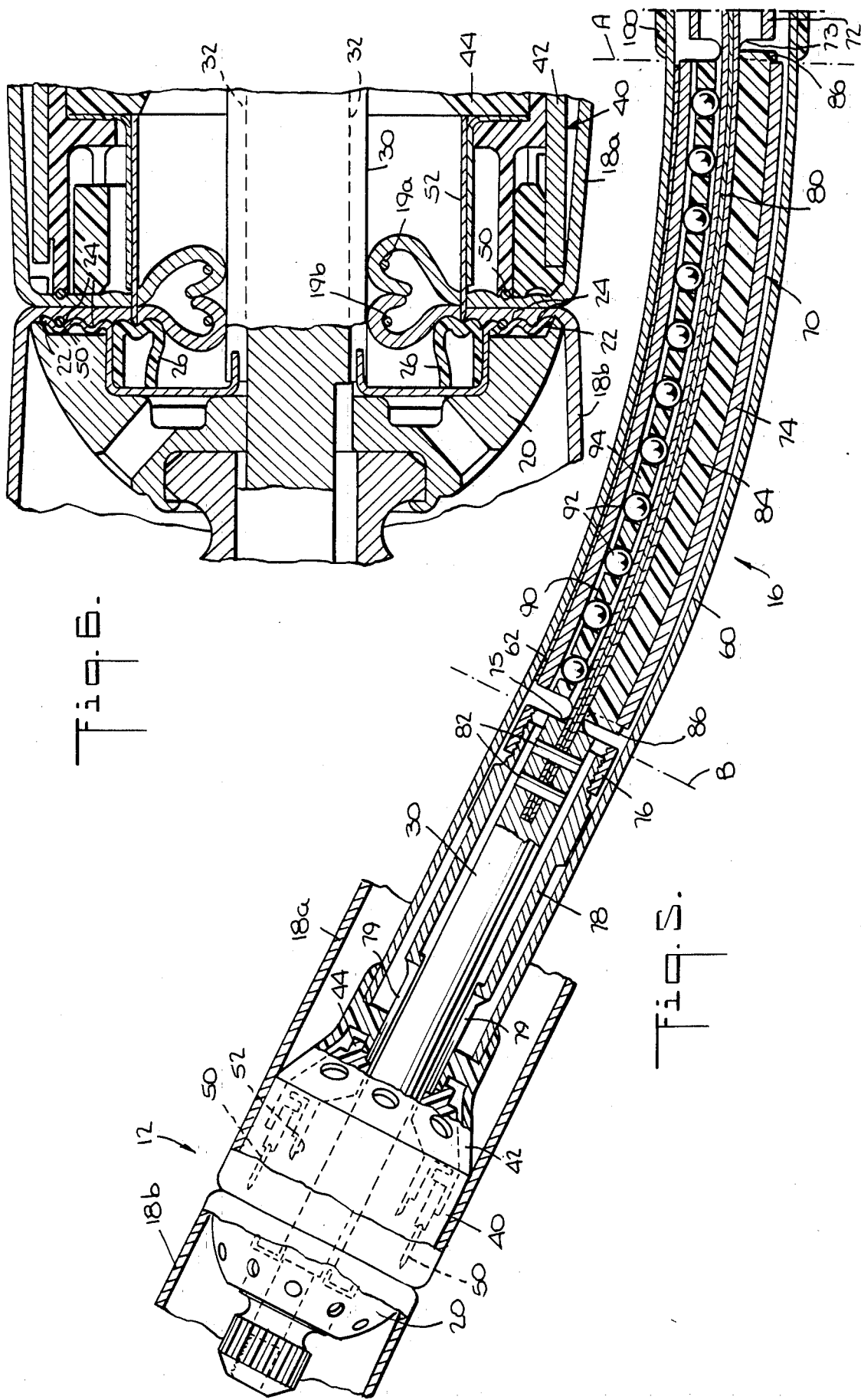

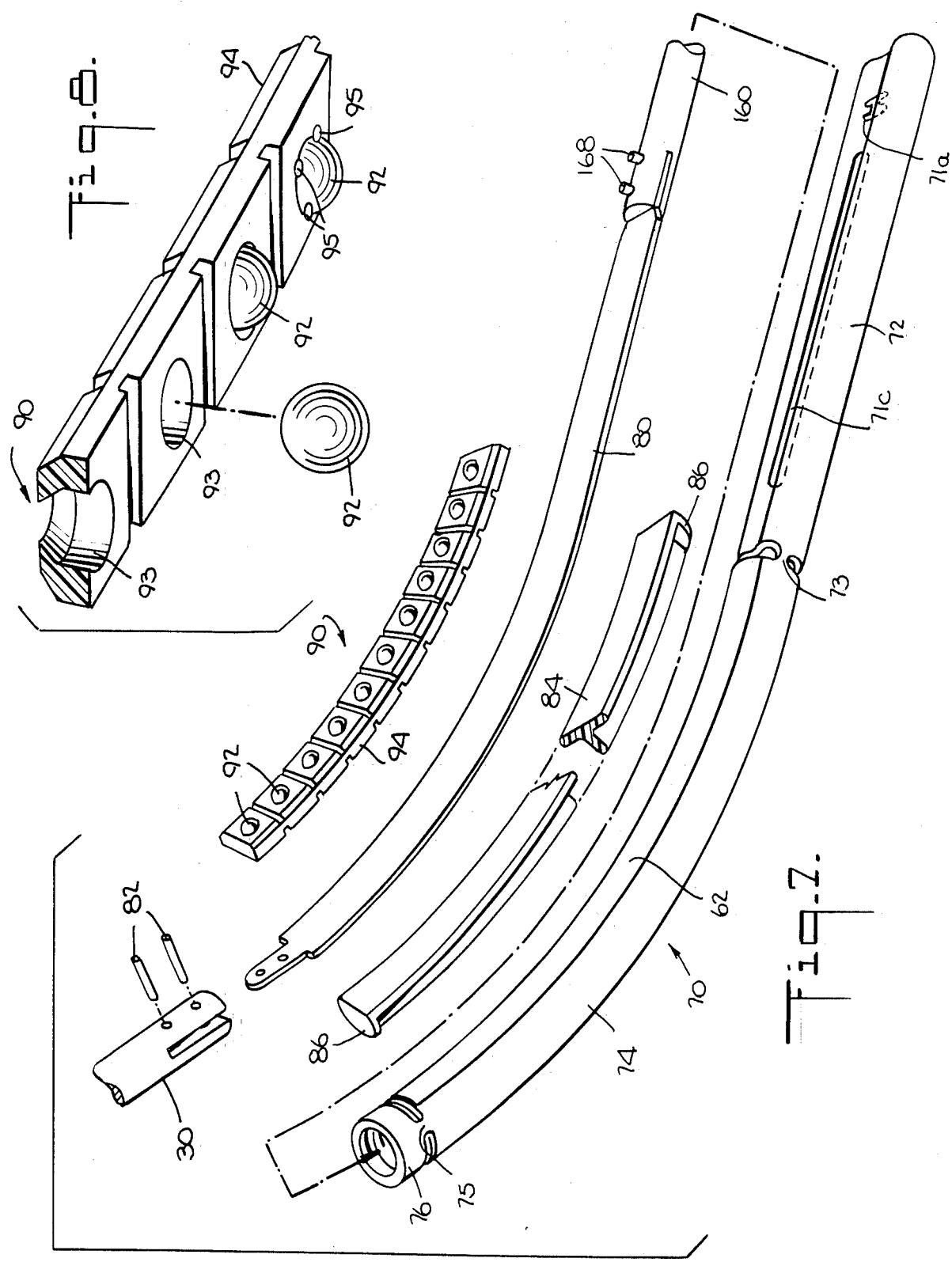

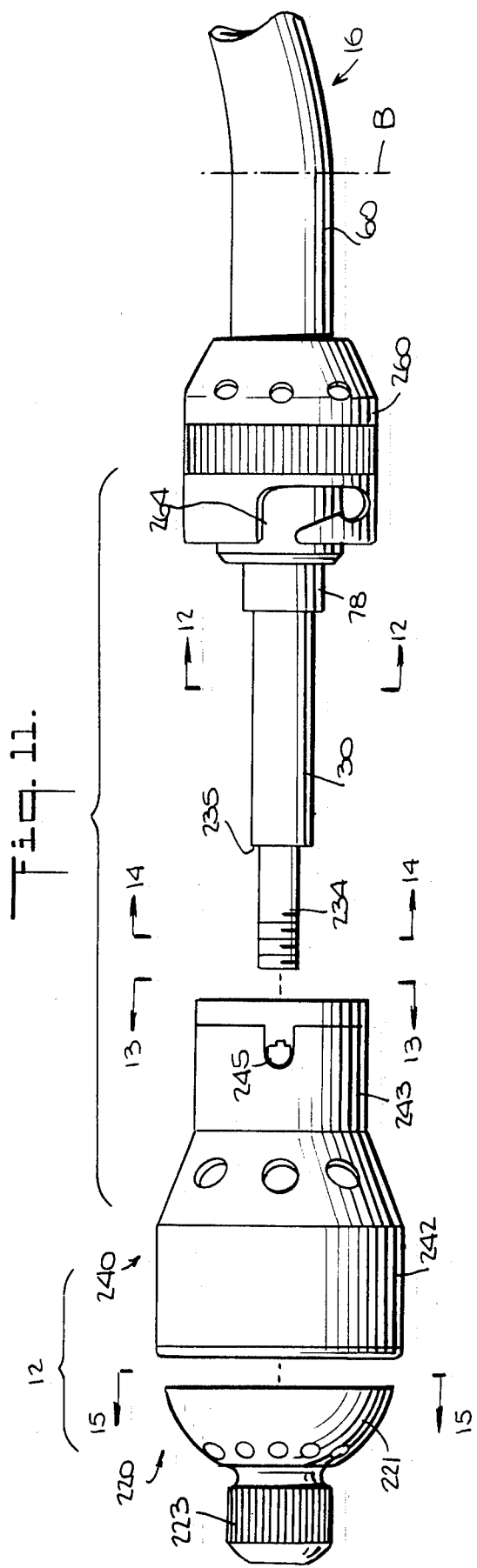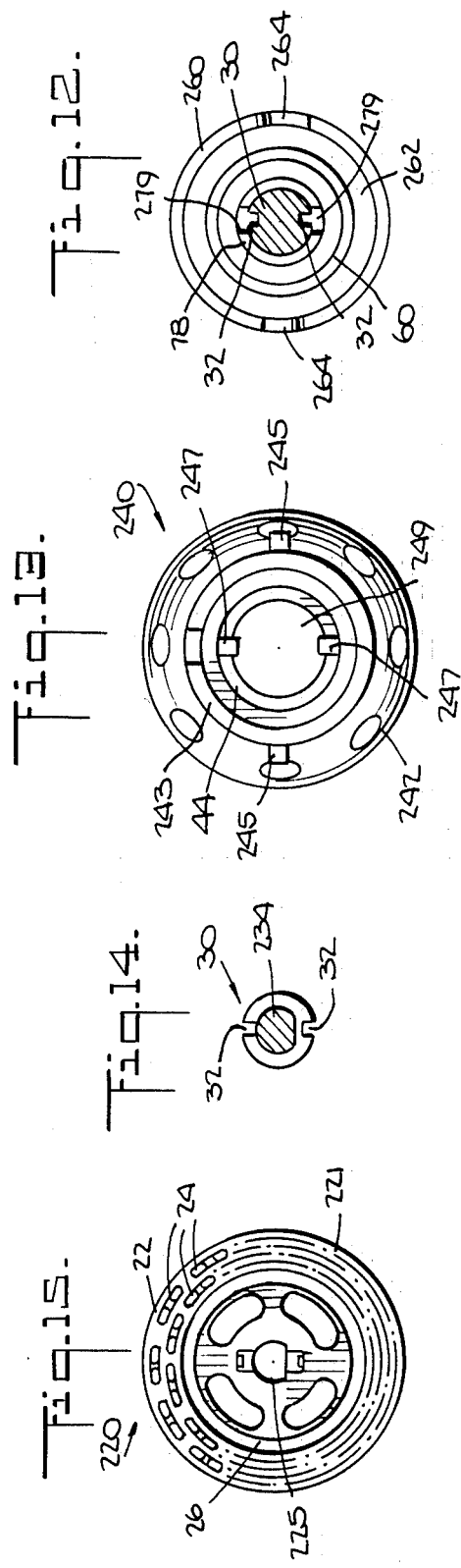

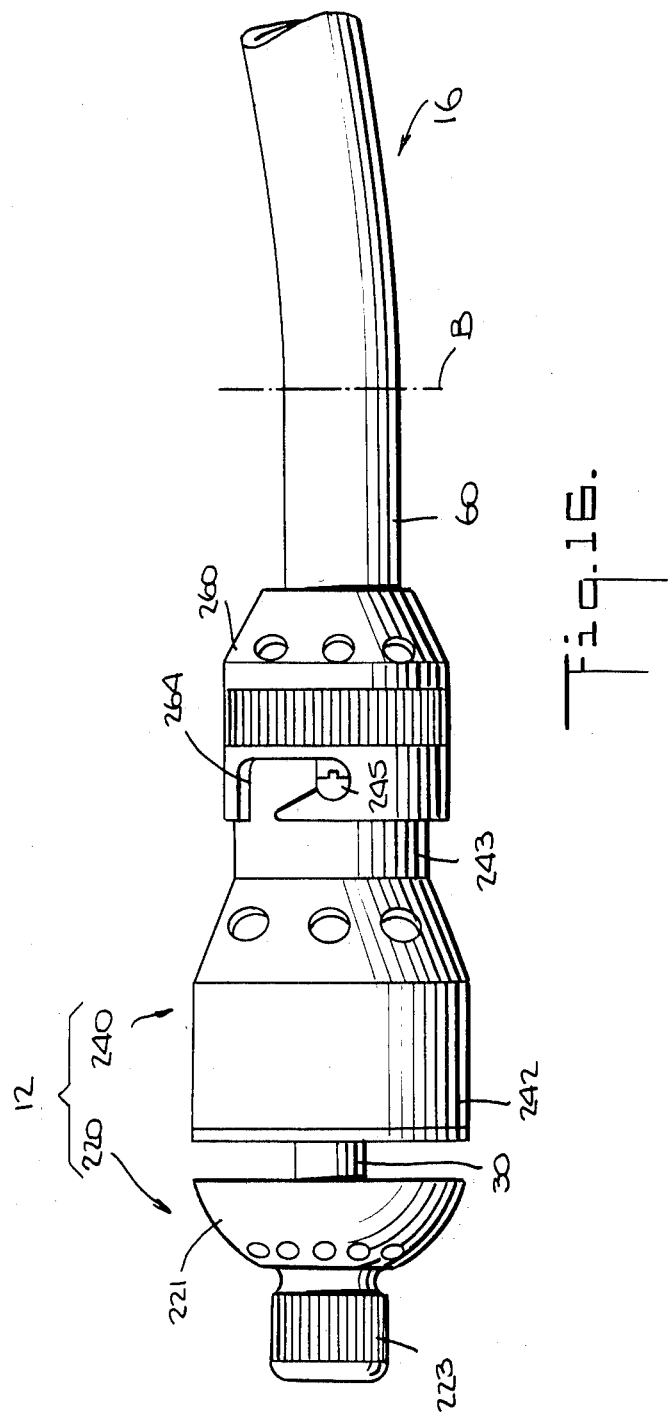

SURGICAL STAPLER APPARATUS WITH CURVED SHAFT

BACKGROUND OF THE INVENTION

This invention relates to surgical stapler apparatus, and more particularly to surgical stapler apparatus having a longitudinally curved shaft intermediate the portion of the apparatus which performs the stapling function and the actuator portion of the apparatus.

There are several known types of surgical staplers in which the stapling function takes place at a location which is relatively remote from the location at which the stapler is held and actuated by the operator. One example of such staplers are the linear closure surgical staplers shown illustratively in Green et al. U.S. Pat. No. 3,494,533. Another example of such staplers are the circular anastomosis surgical staplers shown illustratively in Conta et al. U.S. Pat. No. 4,304,236. Typically, in instruments of the types exemplified by these references, tissue to be stapled is clamped between an anvil assembly and a staple holding assembly, both of which are located at the distal end of the instrument. The clamped tissue is stapled by driving one or more staples from the staple holding assembly so that the ends of the staples pass through the tissue and are clinched by contact with the anvil assembly. The forces required to operate the instrument are applied by the operator of the instrument to one or more actuator elements located at or near the proximal end of the instrument. The distal and proximal portions of the instrument are joined by a longitudinal connecting shaft structure along which the actuating forces and motions are transmitted to the distal operating elements. This type of construction, including relatively widely spaced distal and proximal portions, may be employed for any of several reasons such as the relative inaccessibility of the tissue to be stapled, the need for good visibility of the tissue during stapling, and the like.

In some applications of instruments of the types mentioned above it may be desirable for the longitudinal shaft structure joining the distal and proximal portions of the apparatus to have a longitudinal curve. This may facilitate placement of the instrument in particular body structures, it may facilitate reaching remote or relatively inaccessible stapling sites, or it may allow the staples to be presented at the stapling site at a predetermined angle relative to the operator of the instrument. However, this type of instrument construction means that the actuating forces and motions must be transmitted along a curved structure, which is a considerable complication in the design of the instrument. In addition to requiring that the structure be capable of transmitting actuating forces and motions around a curve, the structure must generally transmit these forces and motions without significant change in curvature ("deflection") of the instrument, and without significantly greater losses due to friction than would be present in a comparable straight instrument. Both the control of deflection and the control of friction losses are much more difficult in a curved instrument than in a comparable straight instrument.

Another complicating factor in designing curved surgical stapling instruments is the increasing interest in surgical instruments which can be economically discarded after use in a single surgical procedure, i.e., so-called disposable instruments. Typically, a disposable instrument is sold in sterile condition in packaging designed to keep the instrument sterile until used. After the instrument has been used in a surgical procedure, it is discarded. In this way all difficulty and expense associated with cleaning, sterilizing, and reloading the instrument are entirely avoided.

For an instrument to be economically disposable after use in only one surgical procedure, however, the cost of the instrument must be relatively low. This generally dictates that as much as possible of the instrument be made of inexpensive materials such as plastics, and that the instrument have the simplest and lightest possible construction. None of these criteria for an economically disposable instrument is readily compatible with the requirements for a curved instrument. For example, the problem of deflection of the curved structure could be reduced or eliminated by using a relatively heavy construction or more expensive stronger materials, but both of these solutions are directly contrary to the needs of a disposable instrument.

In view of the foregoing, it is an object of this invention to provide improved surgical staplers of the type having a curved shaft structure between the distal stapling elements and the proximal actuating elements.

It is another object of this invention to provide economically disposable surgical staplers of the type having a curved shaft structure between the distal stapling elements and the proximal actuating elements.

SUMMARY OF THE INVENTION

These and other objects of the invention are accomplished in accordance with the principles of the invention by providing surgical stapler apparatus including a longitudinally curved shaft assembly for transmitting forces and motions longitudinally between an actuator assembly and a remote stapling assembly, the curved shaft assembly including a longitudinally flexible tension member for transmitting longitudinal tension force, a longitudinally curved compression member for transmitting longitudinal compression force, and means for transmitting force radially of the curved shaft assembly between the flexible tension member and the curved compression member while allowing relative longitudinal motion of those members. The radial force transmitting means makes use of the tendency of the flexible tension member to straighten when transmitting tension force to substantially counteract the tendency of the curved compression member to increase in curvature when simultaneously transmitting compression force. Overall deflection of the curved shaft assembly is therefore greatly reduced or eliminated, even when the shaft assembly is made of relatively inexpensive materials and in a light construction as is desirable to provide an economically disposable instrument.

Further features of the invention, its nature and various advantages will be more apparent from the accompanying drawing and the following detailed description of the invention.

BRIEF DESCRIPTION OF THE DRAWING

FIG. 2 is a longitudinal sectional view of the actuator portion of the apparatus of FIG. 1 showing that apparatus in the condition which produces the maximum separation between the anvil assembly and the staple holding assembly.

FIG. 3 is a fragmented longitudinal sectional view of the portion of the apparatus of FIG. 1 which is not shown in FIG. 2. FIGS. 2 and 3 connect to one another along the left in FIG. 2 and the right in FIG. 3. FIGS. 2 and 3 show the same condition of the apparatus.

FIG. 4 is similar to FIG. 2, but shows the actuator portion of the apparatus in the condition in which the staples are driven.

FIG. 5 is similar to FIG. 3, but shows the elements of the apparatus in the condition corresponding to the actuator condition shown in FIG. 4.

FIG. 6 is an enlarged longitudinal sectional view of a portion of the apparatus of FIGS. 1-5 showing the tissue after it has been stapled and cut by the apparatus.

FIG. 7 is an exploded perspective view of a portion of the apparatus of FIGS. 1-5.

FIG. 8 is an enlarged perspective view of a portion of the apparatus of FIG. 7.

FIG. 9 is a cross sectional view taken along the line 9—9 in FIG. 3.

FIG. 10 is a cross sectional view similar to FIG. 9, but illustrating an alternative embodiment of the invention.

FIG. 11 is a partial elevational view of an alternative embodiment of the invention in which the stapling assembly is removably mounted on the remainder of the apparatus. FIG. 11 shows the elements of the stapling assembly removed from the remaining apparatus.

FIGS. 12-15 are cross sectional views taken along the lines 12—12, 13—13, 14—14, and 15—15, respectively, in FIG. 11.

FIG. 16 is a view similar to FIG. 11 showing the stapling assembly mounted on the remainder of the apparatus.

DETAILED DESCRIPTION OF THE INVENTION

Figure 1:
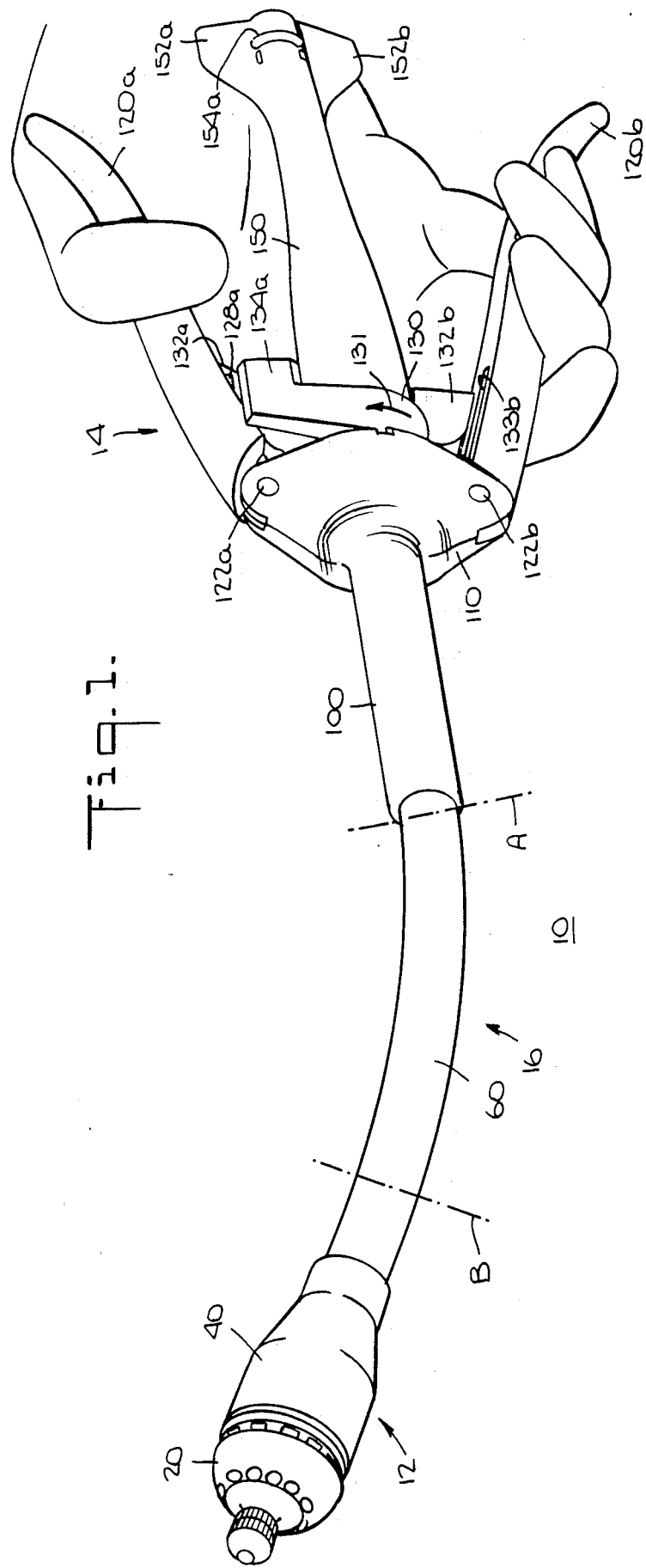
FIG. 1 is a perspective view of a surgical stapler constructed in accordance with this invention.

Although the invention is applicable to other types of surgical staplers as mentioned above, the invention will be fully understood from an explanation of its application to a particular circular anastomosis surgical stapler embodiment. Similarly, although the invention is not limited to disposable instruments (i.e., instruments which are intended to be completely discarded after use in a single surgical procedure), the invention is particularly advantageous in such instruments and will be initially described in the context of such an instrument.

An illustrative embodiment of the invention is the circular anastomosis surgical stapler 10 shown generally in FIG. 1. A typical application of stapler 10 is connecting together two sections of hollow tubular body organ (e.g., two intestinal sections) by means of an annular array of staples which surrounds a lumen or passageway between the interiors of the connected organ sections. Stapler 10 includes distal stapling assembly 12, proximal actuator assembly 14, and longitudinal shaft assembly 16 for connecting the distal and proximal assemblies and for transmitting actuating forces and motions from the actuator assembly to the stapling assembly.

In accordance with the present invention, shaft assembly 16 has a longitudinally curved portion extending from section A to section B. In the particular embodiment shown in the drawing, this curved portion is an arc of a circle and therefore has uniform radius along its length. Although the amount of curvature and the radius of curvature may depend on the type and intended application of the instrument, in a typical instrument intended for joining intestinal sections, the radius of curvature may be about 8 inches and the amount of curvature may be about 26°. In addition to the curved portion, shaft assembly 16 also has two straight portions, each of which is tangent to the curved portion at a respective opposite end of the curved portion.

Stapling assembly 12, which is best described initially with reference to FIG. 3, includes anvil assembly 20 mounted on the distal end of anvil support rod 30 and staple holding assembly 40. Rod 30 is mounted for longitudinal reciprocal motion relative to staple holding assembly 40 so that the spacing between the opposing faces of assemblies 20 and 40 can be varied. As can be seen in FIG. 6, anvil assembly 20 includes annular staple anvil 22 and annular knife anvil or cutting ring 26. Returning to FIG. 3, staple holding assembly 40 includes a housing 42 which initially holds a plurality of U-shaped metal surgical staples 50 arranged in two closely spaced concentric annular rows. The sharply pointed free ends of the legs of each staple 50 point in the distal direction toward staple anvil 22. Staple holding assembly 40 also contains annular tissue cutting knife 52 concentric with and inside the annular array of staples 50. The sharpened tissue cutting edge of knife 52 points in the distal direction toward cutting ring 26. Also included in staple holding assembly 40 is a pusher assembly 44 mounted for longitudinal motion relative to housing 42 for driving staples 50 and knife 52 toward anvil assembly 20.

Anvil assembly 20 and staple holding assembly 40 are both keyed relative to rod 30 so that anvil assembly 20 cannot rotate relative to staple holding assembly 40 about the longitudinal axis of the apparatus. This keeps staples 50 aligned with staple clinching grooves or pockets 24 (FIG. 6) in staple anvil 22 as is desirable for proper clinching of the staples by the anvil.

While not necessary to an understanding of the present invention, additional details regarding the construction of stapling assemblies of the type described above may be found in the above-mentioned Conta et al. application U.S. Pat. No. 4,304,236.

In use in the typical application of joining two intestinal sections together, the instrument is first positioned relative to the tissue as shown in FIG. 3 so that staple holding assembly 40 is inside the end of one intestinal section 18a and anvil assembly 20 is inside the end of the other intestinal section 18-b. The severed ends of organ sections 18a and 18b are secured around rod 30 between assemblies 20 and 40 by means of manually applied purse-string sutures 19a and 19b, respectively. The instrument is then operated as described below to retract anvil supporting rod 30 and thereby draw anvil assembly 20 toward staple holding assembly 40. When anvil supporting rod 30 is fully retracted as shown in FIG. 5, organ sections 18a and 18b are firmly clamped together between the opposing faces of anvil assembly 20 and staple holding assembly 40.

When the tissue of the organ sections has been clamped together as described above, the instrument is further operated as described below to drive the annular array of staples 50 from staple holding assembly 40, through the clamped tissue, and against staple anvil 22 as shown in FIG. 6. Staple anvil 22 clinches the ends of staples 50 so that the two organ sections are securely fastened together by the annular array of staples. The same operation of the instrument which drives the staples also drives knife 52 to cut away the waste or excess tissue inside the annular array of staples and thereby clear the lumen between the connected organ sections.

The joining of the organ sections is now complete and the instrument can be removed as described below.

To remove the instrument from the stapled tissue, anvil assembly 20 is again separated from staple holding assembly 40 so that the tissue is no longer clamped by the instrument. The instrument is then withdrawn by pulling it out through organ section 18a. The excess tissue cut away by knife 52 remains secured to rod 30 by sutures 19a and 19b so that this tissue is removed with the instrument.

Actuator assembly 14 allows the operator of the instrument to produce the above-described operations of stapling assembly 12. Shaft assembly 16 transmits the required forces and motions from actuator assembly 14 to stapling assembly 12.

As can be seen for example in FIGS. 3 and 5, shaft assembly 16 includes a hollow outer shaft tube 60. Staple holding assembly housing 42 is fixedly mounted on the distal end of outer shaft tube 60. The proximal end of outer shaft tube 60 is secured to the main body 100 of actuator assembly 14. As is best seen in FIGS. 1 and 2, actuator body 100 includes a proximal yoke 110 on which proximally extending opposing handles 120a and 120b are ivotally mounted by means of pins 122a and 122b, respectively. Handles 120a and 120b are resiliently biased outwardly by compression coil springs 124a and 124b (FIG. 2) inside yoke 110. As is described in detail below, staples 50 and knife 52 are driven by squeezing handles 120a and 120b together.

To prevent accidental premature squeezing of handles 120a and 120b, safety collar 130 is rotatably mounted on actuator body 100 on the proximal side of pivot pins 122a and 122b. Safety collar 130 includes wings 132a and 132b which project outward underneath handles 120a and 120b, respectively. Safety collar 130 is resiliently biased to rotate in the direction opposite the direction indicated by the arrow 131 in FIG. 1 by springs (not shown) acting between actuator body 100 and collar 130. Safety collar 130 is prevented from rotating farther in this direction than shown in FIG. 1 by inwardly extending lugs 128a and 128b on handles 120a and 120b, respectively. In this position the outer ends of wings 132a and 132b contact the undersides of handles 120a and 120b and prevent the handles from being accidentally squeezed together. Also projecting outward from safety collar 130 are identical tabs 134a and 134b (only tab 134a being visible in the drawing). Each of tabs 134a and 134b is substantially parallel to but spaced from a respective one of wings 132a and 132b on the same side of the wing as the associated lug 128a or 128b. Each tab 134a and 134b extends radially outward farther than wings 132a and 132b so that the ends of tabs 134a and 134b will contact the sides of handles 120a and 120b to stop rotation of safety collar 130 in the direction indicated by arrow 131. When it is desired to release handles 120a and 120b from contact with wings 132a and 132b, either of tabs 134a and 134b is pressed toward the adjacent handle 120a or 120b to rotate safety collar 130 in the direction of arrow 131. When the ends of tabs 134a and 134b contact the sides of handles 120a and 120b, the ends of wings 132a and 132b are respectively aligned with slots 133a and 133b in handles 120a and 120b. Wings 132a and 132b fit into slots 133a and 133b so that handles 120a and 120b can be squeezed together.

On the proximal side of yoke 110 cylindrical nut 140 is mounted for rotation about the longitudinal axis of the instrument by means of annular flange 142 on nut 140 in cooperation with annular channel 112 in body 100. Nut cover 150 is fixedly mounted on nut 140 and extends in the proximal direction between handles 120a and 120b. The proximal end of cover 150 includes laterally extending wings 152a and 152b for facilitating rotation of cover 150 by the operator. Accordingly, nut 140 and cover 150 collectively comprise a wing nut which will be referred to hereinafter as wing nut 150. The proximal end of wing nut 150 also includes two opposite apertures 154a and 154b to allow the operator of the instrument to observe indicator marks 163 inside wing nut 150 as described below.

Inside outer shaft tube 60 and actuator body 100 is a hollow tube 70 (FIGS. 2, 3, and 7) which is mounted for longitudinal motion relative to tube 60. Tube 70 is prevented from rotating about the longitudinal axis of the instrument by projections 126a and 126b on handles 120a and 120b which respectively extend into apertures 71a and 71b in tube 70. The distal end of tube 70 is threadedly connected to hollow extension tube 78 which is also longitudinally movable within outer shaft tube 60. Tubes 70 and 78 constitute a compression member for transmitting a longitudinal compression force (and an associated longitudinal motion) produced by operation of handles 120a and 120b from actuator assembly 14 to staple and knife pusher assembly 44 in staple holding assembly 40. Tubes 70 and 78 therefore transmit from actuator assembly 14 to stapling assembly 12 the force and motion necessary to drive staples 50 and knife 52.

Tube 70 has a straight proximal portion 72 extending from the interior of nut 140 to section A where outer shaft tube 60 begins to curve. At approximately the location of section A tube 70 is transversely notched on each side to leave only two relatively narrow connections 73 from proximal portion 72 to intermediate portions 74. Connections 73 are sufficiently narrow to allow some bending or provide some flexibility in tube 70 about an axis passing through both of connections 73. Connections 73 therefore provide an articulation in tube 70, the axis about which the tube is thus articulated being substantially perpendicular to the plane in which curved shaft assembly 16 lies (i.e., the plane of the paper in FIG. 3, hereinafter referred to as the "plane of curvature" of the apparatus). The material in connections 73 may yield when tube 70 is bent or flexed.

Intermediate portion 74 of tube 70 is curved longitudinally to conform to the surrounding curved portion outer shaft tube 60. This portion of tube 70 extends from connections 73 to approximately section B, where again tube 70 is transversely notched on each side to leave only two relatively narrow connections 75 from intermediate portion 74 to distal portion 76. As in the case of connections 73, connections 75 are sufficiently narrow to allow some bending or provide some flexibility in tube 70 about an axis passing through both of connections 75. Thus connections 75 constitute a second articulation in tube 70 about an axis perpendicular to the plane of curvature of the instrument. Again, the material in connections 75 may yield when tube 70 is bent or flexed, but connections 73 and 75 are both adequately rigid to transmit longitudinal compression force between the adjacent portions of tube 70.

As mentioned above, the distal portion 76 of tube 70 is threadedly connected to straight extension tube 78. The distal end of extension tube 78 extends into staple holding assembly 40 where it contacts staple and knife pusher assembly 44. The distal end of tube 78 contains longitudinal slots 79 allowing keys (not shown) to extend from housing 42 into longitudinal keyways 32 (FIG. 6) in rod 30 without inhibiting the longitudinal motion of tube 78. These keys cooperate with rod 30 to maintain the angular alignment of staple holding assembly 40 relative to anvil assembly 20.

Tube 70 is driven in the distal direction by handle projections 126a and 126b which respectively engage apertures 71a and 71b in the sides of proximal tube portion 72. Thus when safety collar 130 is rotated to release handles 120a and 120b and these handles are squeezed together to the positions shown in broken lines in FIG. 4, tubes 70 and 78 move distally relative to outer shaft tube 60 and staples 50 and knife 52 are driven by pusher assembly 44 as shown in FIG. 6. The articulations in tube 70 provided by connections 73 and 75 allow this limited relative longitudinal motion of tubes 60 and 70 by preventing the straight sections of tube 70 from becoming misaligned with the surrounding straight sections of tube 60.

The relative longitudinal motion of tubes 60 and 70 is preferably aided by the presence of longitudinal spacer member 62 between the outer surface of curved tube section 74 and the opposite inner surface of tube 60. Spacer member 62 is preferably of low friction material such as Teflon (i.e., polytetrafluoroethylene). As is discussed in greater detail below, spacer member 62 transmits force radially in the plane of curvature of the apparatus between curved tube section 74 and the adjacent portion of tube 60, while allowing relative longitudinal motion of these elements. Spacer member 62 may extend to any portion of the annular space between curved tube section 74 and the adjacent portion of tube 60. However, for reasons which will be more apparent later, at least a portion of spacer member 62 preferably extends along the concave side of curved tube section 74 as shown in the drawing.

Inside the proximal portion 72 of tube 70 is a rod 160 which extends from a point on the proximal side of section A, through nut 140, and into the interior of wing nut 150. Rod 160 is mounted for longitudinal reciprocal motion relative to the surrounding elements and is prevented from rotating about its longitudinal axis by transverse pins 168 which extend through rod 160 into longitudinal slots 71c and 71d in tube section 72. An intermediate section 164 of rod 160 threadedly engages nut 140 so that when wing nut 150 is rotated, rod 160 moves in the proximal or distal direction depending on the direction of rotation of wing nut 150. The proximal end portion 162 of rod 160 includes indicator marks 163 on opposite sides of the rod. When anvil assembly 20 is sufficiently close to staple holding assembly 40 so that staples 50 will be properly clinched by the anvil, indicator marks 163 are visible through apertures 154a and 154b in wing nut 150 as shown in FIG. 4.

The linear translation of rod 160 in response to rotation of wing nut 150 is transmitted to rod 30 by flexible band 80 which is mounted in tube 70 for longitudinal reciprocal motion relative to the surrounding elements. Band 80 is typically made up of several thin strips of metal 80a, 80b, 80c to increase its longitudinal flexibility without significantly affecting its tensile strength. The proximal end of flexible band 80 is connected to the distal end of rod 160 by pins 168, and the distal end of band 80 is connected to the proximal end of rod 30 by pins 82. Band 80 is sufficiently flexible to follow the curvature of shaft assembly 16 when pulled longitudinally relative to the remainder of that assembly. The major (i.e., larger) dimension of the rectangular cross section of flexible band 80 is preferably substantially perpendicular to the plane of curvature of the apparatus. A flexible member is preferred for element 80 because the amount of longitudinal motion of element 80 relative to the surrounding elements may be substantial (e.g., 2 inches or more.) Thus a portion of element 80 which is initially in a straight section of shaft assembly 16 may be required to move to a curved section of the shaft assembly and vice versa. This is possible because element 80 is flexible.

In a particularly preferred embodiment of the invention, strip 80c on the convex side of the curved shaft assembly is slightly longer than central strip 80b, and strip 80a on the concave side of the curved shaft assembly is slightly shorter than central strip 80b. In this way the desired amount of longitudinal curvature can be fabricated into band 80 so that it conforms even more easily to the curvature of shaft assembly 16.

Although flexible band 80 may occasionally be required to transmit minor longitudinal compression force (e.g., to move anvil assembly 20 away from staple holding assembly 40), the principal function of flexible band 80 is to act as a tension member for transmitting longitudinal tension force (and accompanying motion) from actuator assembly 14 to stapling assembly 12 for drawing anvil assembly 20 toward staple holding assembly 40 and then holding these two assemblies together to clamp the tissue during stapling and cutting. Because the force required to clamp the tissue may be approximately 50–100 pounds, the force required to drive the staples may be approximately 200 pounds, and the force required to drive the knife may be approximately 175 pounds, it will be apparent that flexible band 80 may be required to transmit tension force of 300 pounds or more during operation of the apparatus. The longitudinal tension force associated with clamping the tissue is resisted or equilibrated by an approximately equal longitudinal compression force in outer shaft tube 60. Similarly, the longitudinal tension force associated with driving the staples and the knife is the result of an approximately equal longitudinal compression force in tube 70.

In order to maintain flexible band 80 approximately in the center of curved tube section 74 while the band is in tension, and in order to transmit force radially between the curved portion of band 80 and the surrounding elements as is desirable to minimize overall distortion of the apparatus in accordance with this invention, spacer means 90 is provided between the concave side of the curved portion of band 80 and the opposite inner surface of curved tube section 74. In addition to keeping band 80 centered in curved tube section 74 and transmitting force radially, spacer means 90 allows relative longitudinal motion of band 80 and tube 70, preferably with minimal friction effects. In the embodiment shown in FIGS. 1–9 spacer means 90 comprises a plurality of ball bearings 92 mounted in a longitudinal race 94 and spaced along the curved portion of shaft assembly 16 (see especially FIGS. 7 and 8). Ball bearings 92 may be made of steel, nylon, Delrin, or any other suitable material. Race 94 is preferably a flexible strip of compatible material such as a plastic material. (FIG. 8 illustrates how ball bearing spacer means 90 may be assembled by inserting each ball bearing 92 in an associated aperture 93 in race 94 and then staking or otherwise deforming race 94 at points 95 to capture the ball in its aperture.)

Ball bearings 92 bear on the central portion of the concave side of flexible band 80 and on the opposite inner surface of curved tube section 74. Ball bearings 92 are sized to keep band 80 substantially in the center of curved tube section 74 even when band 80 is under tension which would otherwise cause it to move toward the concave side of curved tube section 74. Ball bearings 92 also allow curved band 80 to move longitudinally relative to the remainder of the apparatus with very little frictional resistance even though band 80 may be under considerable tension even as the tissue sections to be joined are brought together and clamped between anvil assembly 20 and staple holding assembly 40. Although not shown in the drawing, ball bearing spacer means 90 may move longitudinally in the curved portion of shaft assembly 16 during relative longitudinal motion of tube section 74 and band 80.

An alternative embodiment of spacer means 90 is shown in FIG. 10. In this embodiment, spacer means 90 is a longitudinal member 96 having substantially triangular cross section and extending along substantially the entire length of curved tube section 74. Spacer member 96 is preferably made of a relatively hard, low friction plastic material such as nylon or Teflon. The apex of the triangular cross section of spacer member 96 contacts a relatively small area along the length of the concave side of the curved portion of flexible band 80. The base of the triangular cross section of spacer member 96 contacts the opposite inner surface of curved tube section 74. The position of spacer member 96 is stabilized by a number of outwardly projecting spaced ribs 98. Spacer member 96 keeps flexible band 80 in the center of tube 70 even when band 80 is in tension, and the low friction material of spacer member 96 facilitates relative longitudinal motion of tube section 74 and band 80.

Although flexible band 80 is subject to at most only relatively small longitudinal compression force (e.g., to move anvil assembly 20 away from staple holding assembly 40 after the stapling operation is complete), it may be desirable to provide another spacer element 84 between the convex side of the curved portion of flexible band 80 and the opposite inner surface of curved tube section 74 to keep band 80 centered in tube section 74 even when the band is in compression. As is best seen in FIGS. 7 and 9, spacer 84 typically is a longitudinal member of T-shaped cross section. The top of the T is adjacent the convex side of the curved portion of flexible band 80. The three tips of the T contact the inner surface of curved tube section 74 on the convex side of the tube. Spacer 84 is maintained in the intended longitudinal position by semicircular end pieces 86 which extend radially outward into the notches adjacent connections 73 and 75 in tube 70. Spacer 84 preferably does not fit tightly against the convex surface of the curved portion of flexible band 80, but does prevent flexible band 80 from moving too far from the center of tube 70 and thereby completely releasing spacer means 90 in the event that band 80 is subject to some longitudinal compression force. Spacer 84 is preferably of some inexpensive, relatively low friction plastic material such as nylon.

Considering now the overall operation of the apparatus, the initial position of anvil assembly 20 is approximately the substantially fully retracted position shown in FIG. 1, and the initial position of tube 70 is the proximal position shown in FIGS. 2 and 3. In this condition stapling assembly 12 is passed through organ section 18a until anvil assembly 20 is adjacent the severed end of that organ section. Wing nut 150 is then rotated to cause rod 160 and flexible band 80 to extend rod 30 from staple holding assembly 40 so that purse-string suture 19a can be drawn around rod 30 between assemblies 20 and 40 as shown in FIG. 3. Anvil assembly 20 is inserted in the severed end of organ section 18b and purse-string suture 19b is drawn around rod 30 as also shown in FIG. 3.

When both organ sections have been secured to rod 30 as described above, wing nut 150 is rotated to cause rod 160 and flexible band 80 to retract rod 30 in the proximal direction. During this portion of the operation of the apparatus, flexible band 80 is typically under relatively low tension due to the force required to pull the two organ sections together, but spacer means 90 keeps band 80 moving freely and centrally located in tube 70. As anvil assembly 20 moves toward staple holding assembly 40, indicator marks 163 on the proximal end of rod 160 move toward the proximal end of wing nut 150.

As shown in FIGS. 4 and 5, when anvil assembly 20 is sufficiently close to staple holding assembly 40 that staples 50 can be properly clinched by the anvil, indicator marks 163 become visible in slots 154a and 154b near the proximal end of wing nut 150. This is a visual indication to the operator that the instrument is ready to staple the tissue.

When indicator marks 163 are visible in slots 154a and 154b and it is desired to staple the tissue, safety collar 130 is rotated by means of tabs 134a and 134b to release handles 120a and 120b from engagement by wings 132a and 132b. The tissue is then stapled by squeezing handles 120a and 120b together to the broken line positions shown in FIG. 4. This causes tube 70 to translate in the distal direction as a result of the engagement of handle projections 126a and 126b in tube slots 71a and 71b, respectively. The straight proximal and distal end portions 72 and 76 of tube 70 do not bind against the surrounding elements during longitudinal motion of tube 70 because tube 70 can bend or flex at connections 73 and 75. Spacer means 62 and 90 help assure that tube 70 can move freely relative to tube 60 and flexible band 80.

Distal translation of tube 70 as described above causes corresponding distal translation of tube 78 and staple and knife pusher assembly 44. This in turn drives staples 50 and knife 52 as shown in FIG. 6. The legs of staples 50 pass through the tissue and are clinched by contact with staple anvil 22 to secure the two organ sections together with an annular array of staples. Knife 52 cuts through the excess tissue inside the annular staple array to clear the lumen between the connected organ sections. The stapling procedure is now complete and handles 120a and 120b can be released so that they will return to their initial outer position.

The stapled tissue is released from the apparatus by operating wing nut 150 again to separate anvil assembly 20 from staple holding assembly 40. The instrument is then removed by withdrawing it via organ section 18a. The excess tissue cut away by knife 52 remains secured to rod 30 by sutures 19a and 19b and is therefore removed with the instrument.

The structure of the apparatus described above is particularly advantageous because the forces in the apparatus are distributed and balanced so that the instrument does not tend to distort (particularly by changes in the curvature of shaft assembly 16) during use. When tissue to be stapled is clamped between anvil assembly 20 and staple holding assembly 40, outer shaft tube 60 is subject to a longitudinal compression force (e.g., approximately 50 to 100 pounds) and flexible band 80 is subject to a substantially equal longitudinal tension force. The compression force in tube 60 may tend to cause the curvature of tube 60 to increase. However, this tendency is counteracted by the lateral force applied to the concave side of tube 60 by flexible band 80 acting through spacer means 90, the wall of curved tube section 74, and (if present) spacer means 62. The lateral force referred to is perpendicular to the longitudinal axes of members 60, 70, and 80 and radial of curved shaft assembly 16 in the plane of curvature of that assembly. This force is the radial resultant of the longitudinal tension force transmitted by flexible band 80 along the curved section of shaft assembly 16. (If spacer means 62 is not present, at most only small deflections of tubes 60 and 74 will bring them into lateral force transmitting contact, after which lateral force from flexible band 80 will be applied to tube 60.) The structure is such that the lateral forces described above act substantially continuously along the curved portion of shaft assembly 16. Thus ball bearings 92 provide a large number of closely spaced lateral force transmitting elements between flexible band 80 and tubes 60 and 74, while spacer member 96 in the alternative embodiment shown in FIG. 10 provides continuous transmission of lateral force between elements 60, 74, and 80. As mentioned above, the lateral force transmitted from the curved section of flexible band 80 to the curved section of tube 60 substantially reduces or eliminates any tendency of the curvature of shaft assembly 16 to change in response to the forces required to clamp the tissue in the instrument.

When staples 50 and knife 52 are driven, tube 70 is subject to a longitudinal compression force, which in some embodiments may be as high as 200 pounds or more. An equal longitudinal tension force is produced in flexible band 80. Because the tissue clamping forces mentioned in the preceding paragraph are still being applied while these stapling and cutting forces are being produced, the tension force in flexible band 80 due to stapling and cutting is added to the tension force in band 80 due to tissue clamping.

Like the curved portion of outer shaft tube 60, the curvature of curved section 74 of tube 70 may tend to increase as a result of the longitudinal compression force applied to it. Again, however, this tendency is substantially counteracted by the lateral force applied to the concave side of tube section 74 from the curved portion of flexible band 80. This lateral force is transmitted from band 80 to tube section 74 in a substantially continuous manner by spacer means 90, i.e., ball bearings 92 in the embodiment of FIGS. 1-9 or spacer member 96 in the embodiment of FIG. 10. As in the case of the tissue clamping forces, as the compression force in tube 70 increases, the tension force in flexible band 80 increases correspondingly. This means that as the tendency of tube section 74 to increase in curvature becomes greater in response to increasing compression force in that tube section, this tendency is counteracted more strongly by a corresponding increase in the lateral force applied to tube section 74 from flexible band 80. Any tendency of the curvature of the instrument to change as a result of the forces required to staple and cut the tissue is thereby substantially reduced or eliminated.

The inherent resistance of the instrument design of this invention to changes in curvature is especially important in the case of instruments intended to be disposable after use in a single surgical procedure. In order to be economically disposable, such instruments must generally be made of relatively inexpensive materials and in the lightest possible construction. For example, in a disposable instrument of the type described above, most of the larger pieces of actuator assembly 14 are typically made of plastic, outer shaft tube 60 is typically thin aluminum tubing, and tube 70 and flexible band 80 are also typically made of relatively thin metal elements. The stiffness of shaft assembly 16 in an instrument of this construction is relatively low, and design of the instrument in accordance with the principles of this invention is particularly helpful in reducing or eliminating distortion of the shaft assembly in response to the forces produced in the instrument during tissue clamping, stapling, and cutting.

The shaft assembly in apparatus constructed in accordance with this invention need not have only one longitudinally curved section of uniform radius. Alternatively, the shaft assembly could have several longitudinally curved sections arranged end-to-end, each with a different radius of curvature. In that event, an articulation similar to articulation 73 or 75 would be provided in tube 70 adjacent the location of each change in curvature of the shaft assembly. Similarly, several longitudinally curved sections could be interspersed with straight sections, articulations being provided in tube 70 adjacent each transition between straight and curved sections.

Although the invention has been described above in its application to a totally disposable instrument, the invention is not limited to such instruments. For example, FIGS. 11-16 illustrate an alternative embodiment of the invention in which stapling assembly 12 is removably mounted on the distal end of curved shaft assembly 16. In this way stapling assembly 12 can be made as a disposable item, while the balance of the apparatus (i.e., actuator assembly 14 and shaft assembly 16) can be made as a permanent and reusable instrument.

Stapling assembly 12 in FIGS. 11-16 may be generally similar to the corresponding elements in the apparatus shown, for example, in FIG. 41 of the abovementioned Conta et al. U.S. Pat. No. 4,304,236. Except for the removable mounting, this portion of the Conta et al. apparatus is also similar to stapling assembly 12 in the embodiments of FIGS. 1-10 herein. Accordingly, the details of stapling assembly 12 will not be repeated here. The manner in which stapling assembly 12 is removably mounted on the distal end of shaft assembly 16 in FIGS. 11-16 may also be similar to the manner in which the stapling assembly in the Conta et al. apparatus is removably mounted on the Conta et al. instrument. Reference can therefore be made to the Conta et al. patent for additional details regarding the stapling assembly mounting. These additional details are not necessary for an understanding of the present invention.

As in the Conta et al. apparatus, a retention ring 260 is mounted on outer shaft tube 60 near the distal end of that tube for limited rotational movement about the longitudinal axis of the instrument. An annular space 262 is provided between the distal end of tube 60 and the distal end of retention ring 260 for receiving the proximal end 243 of the housing 242 of staple holding assembly 240. The distal end of retention ring 260 includes two diametrically opposite L-shaped slots 264 for receiving and engaging two diametrically opposite, radially outwardly projecting lugs 245 on the proximal portion 243 of staple holding assembly housing 242.

The distal end of extension tube 78 extends slightly beyond the distal end of outer shaft tube 60, and the distal end of rod 30 extends beyond the distal end of extension tube 78. The distal end portions of elements 30 and 78 have diametrically opposite, radially aligned, longitudinal channels or slots 32 and 279, respectively, for receiving two diametrically opposite, radially inwardly projecting keys 247 on the proximal portion 243 of staple holding assembly housing 242. Keys 247 pass through slots 279 and engage channels 32 to fix the angular orientation of staple holding assembly 240 relative to rod 30. Staple holding assembly 240 has a central longitudinal aperture 249 through which the distal portion of rod 30 passes freely. When staple holding assembly 240 is mounted on shaft assembly 16, the distal end of extension tube 78 contacts or is immediately adjacent the proximal surface of pusher assembly 44 inside assembly 240.

Staple holding assembly 240 is mounted on the distal end of shaft assembly 16 by aligning keys 247 with channels 32 and sliding assembly 240 along rod 30 until the distal end 243 of housing 242 is in the annular space 262 inside the distal end of retention ring 260. In this position of staple holding assembly 240, lugs 245 have entered the longitudinally extending portions of L-shaped slots 264 in retention ring 260. Retention ring 260 is then rotated about the longitudinal axis of the instrument so that the distal sides of the circumferentially extending portions of L-shaped slots 264 firmly engage lugs 245 and thereby secure staple holding assembly 240 to shaft assembly 16 as shown in FIG. 16. The proximal surface portions of staple holding assembly 240 are designed to mate with adjacent distal surface portions of outer shaft tube 60 so that staple holding assembly 240 cannot wobble relative to shaft assembly 16.

As in the above-mentioned Conta et al. apparatus, anvil assembly 220 includes a housing 221 and an internally threaded nut 223 rotatably mounted on the distal side of the housing. Housing 221 carries concentric annular staple anvil 22 and knife anvil or cutting ring 26. A D-shaped aperture 225 passes longitudinally through the center of housing 221 and communicates with the threaded interior (not shown) of nut 223. Anvil assembly 220 fits on the threaded distal end portion 234 of rod 30. End portion 234 has a D-shaped cross section which mates with D-shaped aperture 225 in anvil assembly housing 221 to prevent housing 221 (and therefore anvil members 22 and 26) from rotating about the longitudinal axis of the apparatus. This keeps staple anvil pockets 24 angularly aligned with corresponding staples in staple holding assembly 240. Nut 223 threadedly engages the threaded distal end of rod portion 234 to secure the anvil assembly to the apparatus. Nut 223 is screwed down until housing 221 contacts shoulder 235 at the proximal end of rod portion 234.

When staple holding assembly 240 and anvil assembly 220 have been mounted on the distal end of shaft assembly 16, the apparatus is ready for use in the same way that the apparatus of FIGS. 1–10 is used. The remainder of the apparatus may be identical to the corresponding portions of the previously discussed embodiments. Thus the portion of shaft assembly 16 on the proximal side of retention ring 260 may be identical to the corresponding portion of shaft assembly 16 in FIGS. 1–10, and the actuator assembly (not shown in FIGS. 11–16) may be identical to actuator assembly 14 in FIGS. 1–10. Of course, somewhat different materials (e.g., stainless steel rather than plastic or thin aluminum) may be chosen for certain parts of the actuator and shaft assemblies to make these assemblies more permanent if this portion of the apparatus is designed to be reusable.

If the actuator and shaft assemblies are reusable, staple holding assembly 240 and anvil assembly 220 are typically removed and discarded after use in a surgical procedure. Anvil assembly 220 is removed by unscrewing nut 223 until it releases rod 30 so that anvil assembly 220 can be pulled off the end of the rod. Retention ring 260 is then rotated to release lugs 245 from the circumferential portions of L-shaped slots 264 so that staple holding assembly 240 can be pulled off the end of shaft assembly 16. The apparatus can be used again when fresh staple holding and anvil assemblies 240 and 220 are mounted on the shaft assembly.

It will be understood that the foregoing is only illustrative of the principles of the invention, and that various modifications can be made by those skilled in the art without departing from the scope and spirit of the invention. For example, the particular actuator assembly configuration shown is not critical and other actuator arrangements can be used if desired. One possible alternative is an actuator in which the handles for driving tube 70 are substantially perpendicular to the longitudinal axis of the instrument. Such actuators are well-known for instruments of this type, as shown, for example in the above-mentioned Conta et al. patent.

I claim:

1. Apparatus for applying surgical staples to body tissue comprising:

an anvil assembly;

a staple holding assembly containing a plurality of surgical staples and including (a) a first body, (b) anvil support means for supporting the anvil assembly for motion relative to the first body to allow the tissue to be stapled to be clamped between the anvil assembly and the first body, and (c) pusher means movably mounted relative to the first body for driving the staples from the staple holding assembly through the clamped tissue and against the anvil assembly;

an actuator assembly remote from the staple holding assembly and including (a) a second body, (b) first actuator means movably mounted on the second body for controlling the anvil support means, and (c) second actuator meaans movably mounted on the second body for controlling the pusher means; and a longitudinal shaft assembly including (a) a rigid longitudinal shaft member connected at one end to the first body and at the other end to the second body, the shaft member being a hollow tube having a longitudinally curved section intermediate its ends, at least a portion of the curved section having uniform radius, the shaft member also including a longitudinally straight section substantially tangent to one end of the portion of uniform radius, (b) a longitudinal tension member disposed in the shaft member for longitudinal motion relative to the shaft member for transmitting longitudinal tension force and longitudinal motion from the first actuator means to the anvil support means to pull the anvil assembly toward the first body to clamp the tissue and to resist the force of the staples being driven through the tissue and against the anvil assembly, the tension member being longitudinally flexible and longitudinally inextensible and incompressible, (c) a longitudinal compression member disposed in the shaft member for longitudinal motion relative to the shaft member for transmitting longitudinal compression force and longitudinal motion from the second actuator means to the pusher means to cause the pusher means to drive the staples, the compression member being a longitudinally inextensible and incompressible hollow tube concentric with the shaft member tube, the compression member tube being articulated adjacent the point of tangency of the straight section of the shaft assembly to permit some relative longitudinal motion between the tubes without binding of the tubes relative to one another, the tension member being disposed in the interior of the compression member tube, and (d) means associated with the curved section of the shaft assembly for maintaining each of the tension member and the compression member coaxial with respective predetermined longitudinal axes in the shaft member while allowing the tension member and the compression member to move longitudinally relative to one another and relative to the shaft member, the means for maintaining comprising spacer means between the concave side of the tension member and the opposite inner surface of the compression member tube in the curved section of the shaft assembly.

2. The apparatus defined in claim 1 wherein the compression member tube is articulated by means of opposing transverse notches in the concave and convex sides of the tube.

3. Apparatus for joining two hollow organ sections with an annular array of surgical staples around a hollow lumen between the organ sections comprising:

an anvil assembly;

a staple holding assembly including (a) a housing containing a plurality of surgical staples in an annular array, (b) a rod passing through the interior of the annular array for supporting the anvil assembly for motion relative to the staple holding assembly to allow the tissue of the organ sections to be stapled to be clamped between the anvil assembly and the housing, and (c) pusher means movably mounted in the housing for driving the staples from the housing through the clamped tissue and against the anvil assembly to clinch the staples and staple the tissue;

an actuator assembly remote from the staple holding assembly and including (a) a main body, (b) a first actuator movably mounted on the main body for controlling the motion of the rod, (c) a second actuator movably mounted on the main body for controlling the motion of the pusher means, and (d) indicator means movably mounted on the main body and operated by the first actuator for providing an indication of the spacing between the anvil assembly and the housing by means of the relative positions of the indicator means and the main body;

a longitudinal hollow tubular shaft for supporting the housing relative to the main body, the shaft being substantially rigid and having a longitudinally curved section intermediate the main body and the housing, at least a portion of the curved section of the shaft having uniform radius, the shaft also including a straight section tangent to one end of the portion of uniform radius;

a longitudinally flexible tension member disposed in the shaft for transmitting longitudinal tension force and longitudinal motion relative to the shaft from the first actuator to the rod to pull the anvil assembly toward the housing to clamp the tissue and to resist the force of the staples being driven through the tissue and against the anvil assembly, the tension member being longitudinally inextensible;

a longitudinal compression member disposed in the shaft around the tension member for transmitting longitudinal compression force and longitudinal motion relative to both the tension member and the shaft from the second actuator to the pusher means to drive the staples, the compression member being a longitudinally incompressible hollow tube concentric with the shaft, the tube being articulated adjacent the point of tangency of the straight section to facilitate relative longitudinal motion of the tube and the shaft; and means disposed in the shaft for maintaining the tension member and the compression member coaxial with respective predetermined longitudinal axis in the shaft while llowing relative longitudinal motion of the tension member and the compression member so that motion of the first actuator relative to the main body produces corresponding motion of the anvil assembly relative to the housing so that the indicator means provides an accurate indication of the spacing between the anvil assembly and the housing, the means for maintaining comprising spacer means between the concve side of the tension member and the opposite inner surface of the tube.

* * * * *